United States Patent [19]

Gelius

[11] 4,349,250

[45] Sep. 14, 1982

[54] PROCESS AND APPARATUS FOR THE DYNAMIC OR STATIC PERIMETRY OF THE HUMAN EYE

[75] Inventor: Siegfried Gelius, Munich, Fed. Rep. of Germany

[73] Assignee: Optische Werke G. Rodenstock, Munich, Fed. Rep. of Germany

[21] Appl. No.: 28,691

[22] Filed: Apr. 10, 1979

[30] Foreign Application Priority Data

Apr. 11, 1978 [DE] Fed. Rep. of Germany ....... 2815657

[51] Int. Cl.³ .............................................. A61B 3/06
[52] U.S. Cl. ......................................... 351/32; 351/39
[58] Field of Search ........................ 351/23, 24, 32, 39

[56] References Cited

U.S. PATENT DOCUMENTS 3,984,156 10/1976 Jernigan ............................ 351/39 X Primary Examiner—Paul A. Sacher
Attorney, Agent, or Firm—Craig and Antonelli

[57] ABSTRACT

A process and apparatus for dynamic or static perimetry of the human eye wherein topographical measuring threshold values of eye sensitivity for the eye being tested are obtained and are electronically compared with stored standard values of eye sensitivity corresponding to the testing conditions. An indication is provided of deviations between the measured values and the stored standard values. The apparatus includes a perimetry device, a computer for storing the standard values and at least one program for controlling the perimetry device and for comparing the measured values with the stored standard values and a display arrangement for displaying the values and deviations.

18 Claims, 5 Drawing Figures

ISOPTER COMPARISON

PROCESS AND APPARATUS FOR THE DYNAMIC OR STATIC PERIMETRY OF THE HUMAN EYE

The present invention relates to a process and apparatus for dynamic or static perimetry of the human eye, wherein topographically determined threshold values of eye sensitivity are recorded in graphic or tabular form.

A large number of processes and devices have been known for testing the visual field of the human eye, wherein the eye to be tested is offered, on planar or curved display areas, within the framework of dynamic or kinetic perimetry individual, movable light targets or visual stimuli or in case of static perimetry one or simultaneously several, stationary light targets or visual stimuli. Such processes and devices are described for example, in various publications and brochures, such as "Single and Multiple Stimulus Static Perimetry in Glaucoma; the Two Phases of Perimetry, " by E. L. Greve, Dr. W. Junk B. V. publishers (1973); "An Automatic Static Perimeter, Design and Pilot Study" by A. Heijl and C. E. T. Krakaw, *ACTA Ophthalmologica*, Vol. 53, 1975, p. 293–310; "Probleme der automatischen Perimetrie" by M. Zingirian and V. Tagliasco (1977); and the brochures "Octopus" by Intergray AG of Switzerland and "Goldmann Perimeter 940" by Hagg-Sheit AG of Switzerland.

The test result utilizing such processes and devices is in each instance a graphic or tabular representation of the test results in dependence on the respectively utilized testing procedure. The evaluation of such test results, i.e. the determination of deviations from values normal for the given test, requires from the person carrying out the test voluminous expert knowledge as well as intensive involvement with the test results.

It is therefore an object of the present invention to provide a process and apparatus for the dynamic or static perimetry of the human eye wherein individually measured sensitivity values are immediately correlated with the normal sensitivity of a healthy eye and wherein deviations from normal sensitivity are recognizable at once by graphic or numerical display.

According to the present invention, a process for dynamic or static perimetry of the human eye is provided including the steps of measuring threshold values of eye sensitivity, recording the measured values in graphic or tabular form, electronically comparing the measured values with stored standard values associated with the testing conditions for the measured values, and displaying deviations between the measured values and stored values.

The present invention also provides apparatus for carrying out the process for dynamic or static perimetry of the human eye including a perimeter, a control arrangement for controlling the perimeter in accordance with desired conditions, a program control for effecting perimeter operation in accordance with a predetermined program, a storing arrangement for storing the measured values of the tested, a computer for comparing the measured values with stored standard values corresponding to the same test conditions, and a display arrangement for displaying deviations between the measured values and stored values.

In accordance with the present invention, the process steps for determining a certain grouping of sensitivity values of the eye being tested, or the geometric arrangement of such values, can take place in accordance with a program. Each testing program is associated with standard values which are stored electronically and recalled within the scope of the testing program for comparison purposes. The individual testing programs, as well as the standard values associated therewith can correspond to personal characteristics of the person to be tested, especially the age or the individual, general sensitivity level of such person. Within the scope of the initially programmed testing programs, size, brightness, display period, and color of the offered light targets can be variable. Also, the brightness of the background can be chosen to be different.

In connection with each testing program, standard values correlated in accordance with the present invention are stored electronically. These stored values are values which have been determined statistically and correspond to the average sensitivity distribution of a rather large collective group of persons. To determined the individual sensitivity values, it is possible to utilize convention perimeter devices for conducting static or dynamic perimetry. The standard stored values are then compared with the individual values measured in the test by conventional electronic components such as a computer.

The stored standard values can be correlated with specific test runs in the form of series of values. Also, the standard values can be distributed point-by-point in any desired interstitial width over the visual field of one eye and in mirror-image symmetry over the visual field of the other eye. Specific values correlated with the selected testing program can be recalled from these stored standard values. Additionally, values lying between stored values can be interpolated.

In connection with individually measured values obtained during the test, the standard values in closest proximity thereto can be recalled, and, if these closest values do not conform with the standard values statistically associated with the person being tested, diagnostic conclusions can be drawn. The representation of the recalled, stored standard values, as well as of the individually measured values takes place in the same way and on the same scale as, for example, a succession of dots or a train of curves in a diagram or a numerical series of values so as to provide a display indicating deviations, the measured and stored standard values. The values individually measured during an examination can additionally be stored separately and can serve for documentation during subsequent comparison measurements, for example, when observing the course of a disease.

These and further objects, features and advantages of the present invention will become more obvious from the following description when taken in connection with the accompanying drawings; wherein FIG. 1 shows axially parallel meridian section through the pole representing one form of display of values in accordance with the present invention;

Figure 1:
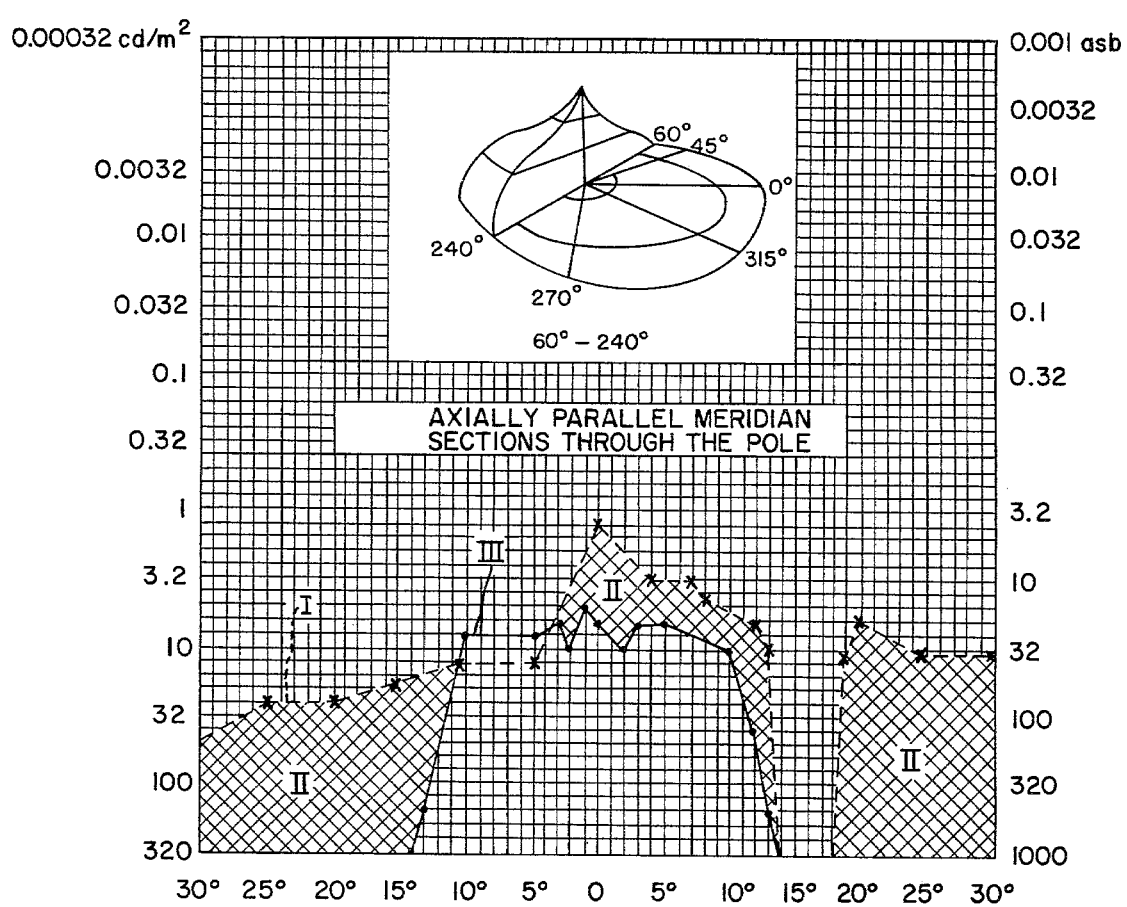

Referring now to the drawings, FIG. 1 shows an axially parallel meridian section through the pole in a graphic representation of the type utilized for perimetry. The dashed line I indicates a normal curve resulting in case of static perimetry in the horizontal meridian 0°–180° under photopic luminosity conditions as represented by the physical units "cd/m$^2$" and "asb" based upon previously obtained measurements for a normal eye with the measurement values being indicated by "X" in the graph. The solid line curve corresponds, for example, to an actual, statically measured eye sensitivity for an eye being tested, wherein the measured values for an eye with a deficiency are indicated by a "." in the graph. The cross-hatched field II corresponds to the deviation of the measured values from the normal or standard values and thus to the sensitivity deficit of the eye being tested. In the area of the curve train III, the measured sensitivity for the eye tested is above the normal values to be expected.

Figure 2:
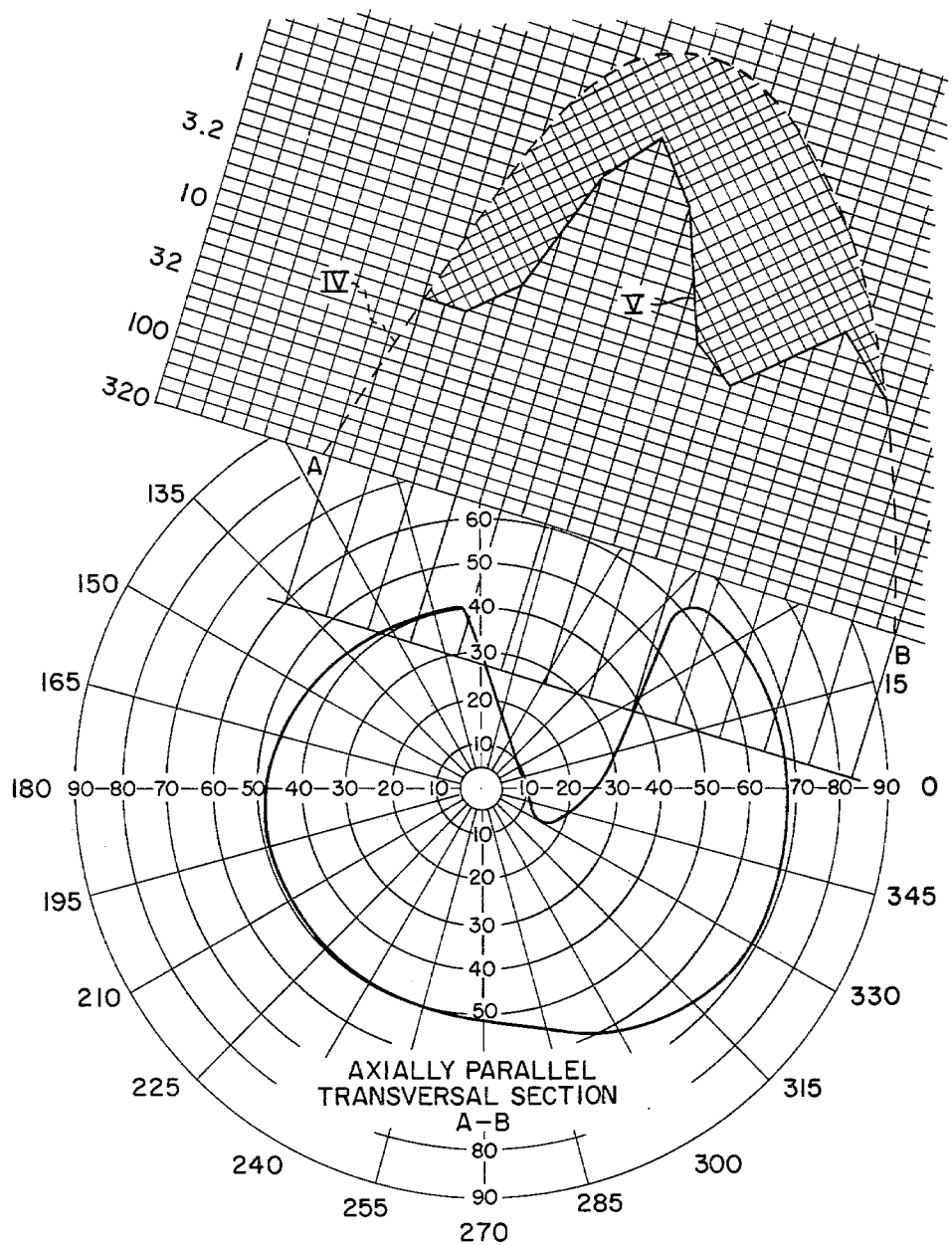
FIG. 2 shows an axially parallel transversal section representing another form of display of values in accordance with the present invention.

FIG. 2 shows an axially parallel transversal section along a straight line extending through points A and B, in conjunction with a recording of isopter, i.e. horizontal sections through the up-and-down range of sensitivity of the eye, clearly indicating failures in the visual field. The dashed line curve IV represents the normal sensitivity curve along the straight line from A to B, in accordance with previously obtained measurements, whereas the solid line curve V indicates the measured sensitivity curve for the eye tested in the same direction. The cross-hatched field represents the differences between the two curves.

The length of distance A−B and the position of the measuring points distributed along the straight line is derived from the scale of the isopter diagram. A−B is the abscissa in the customary, static sensitivity diagram with the threshold value sensitivities being plotted as the ordinate on a logarithmic scale.

Figure 3:
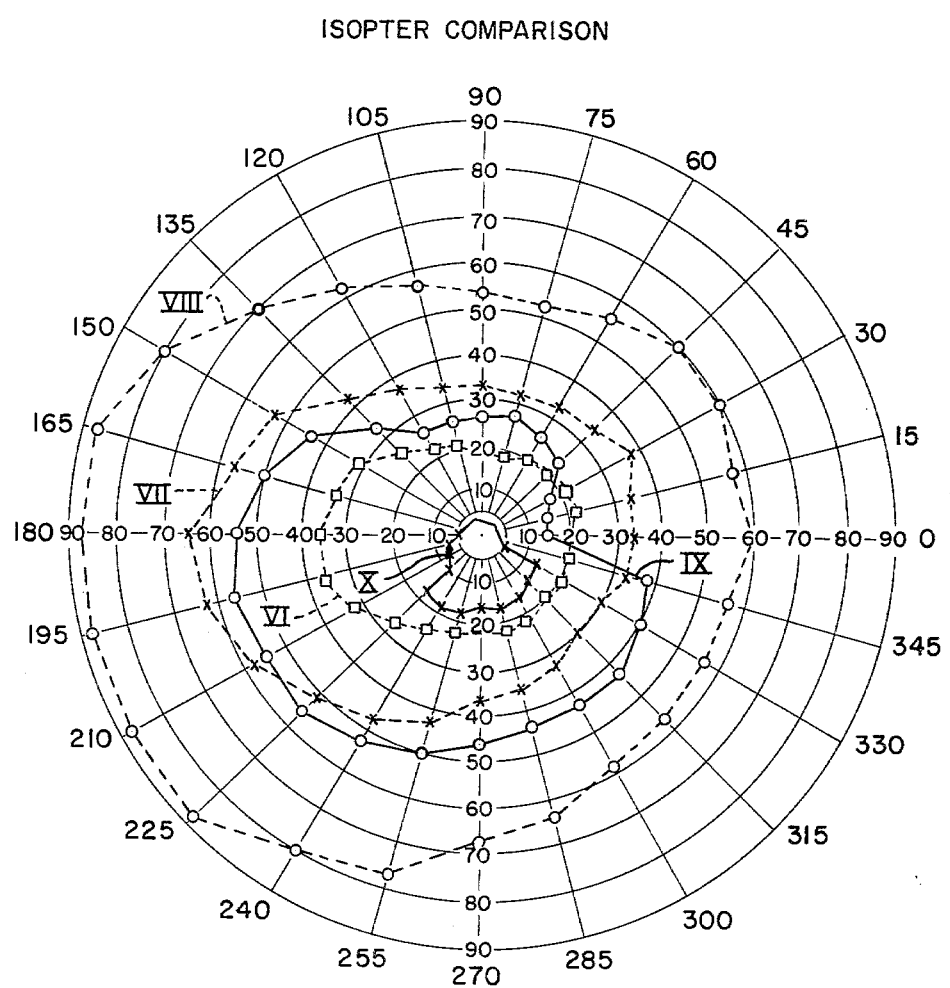
FIG. 3 shows an isopter diagram representing still another form of display of values in accordance with the present invention.

FIG. 3 shows, in a diagram, three isopter curves VI, VII, and VIII illustrated in broken lines, recorded with different intensities, for example, according to Goldmann, and stored as standard or normal values. The individually recorded isopters IX and X, illustrated in solid lines for an eye being tested, readily demonstrate the deviation from comparable standard values.

Figure 4:
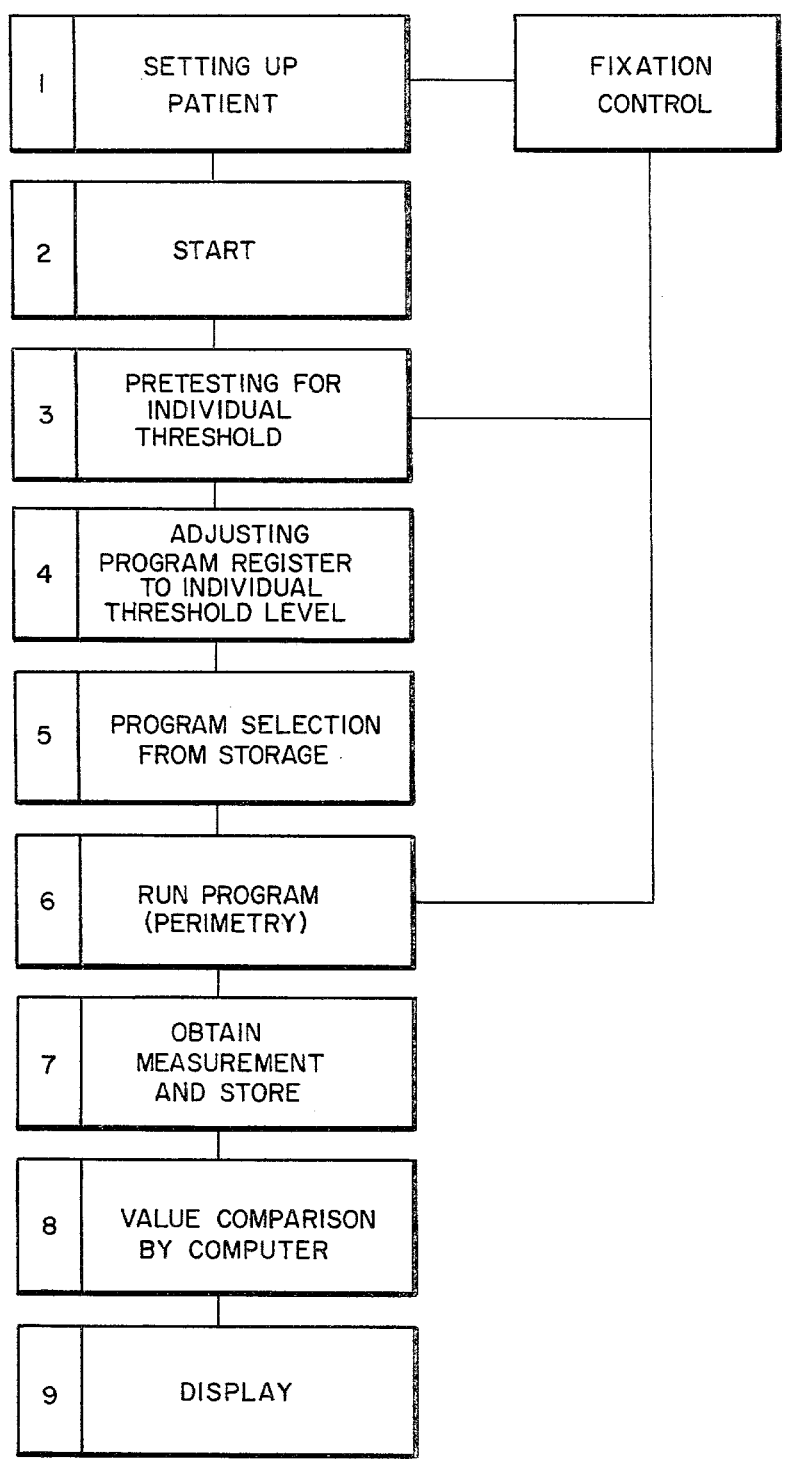
FIG. 4 is a flow diagram of the process in accordance with the present invention.
Figure 5:
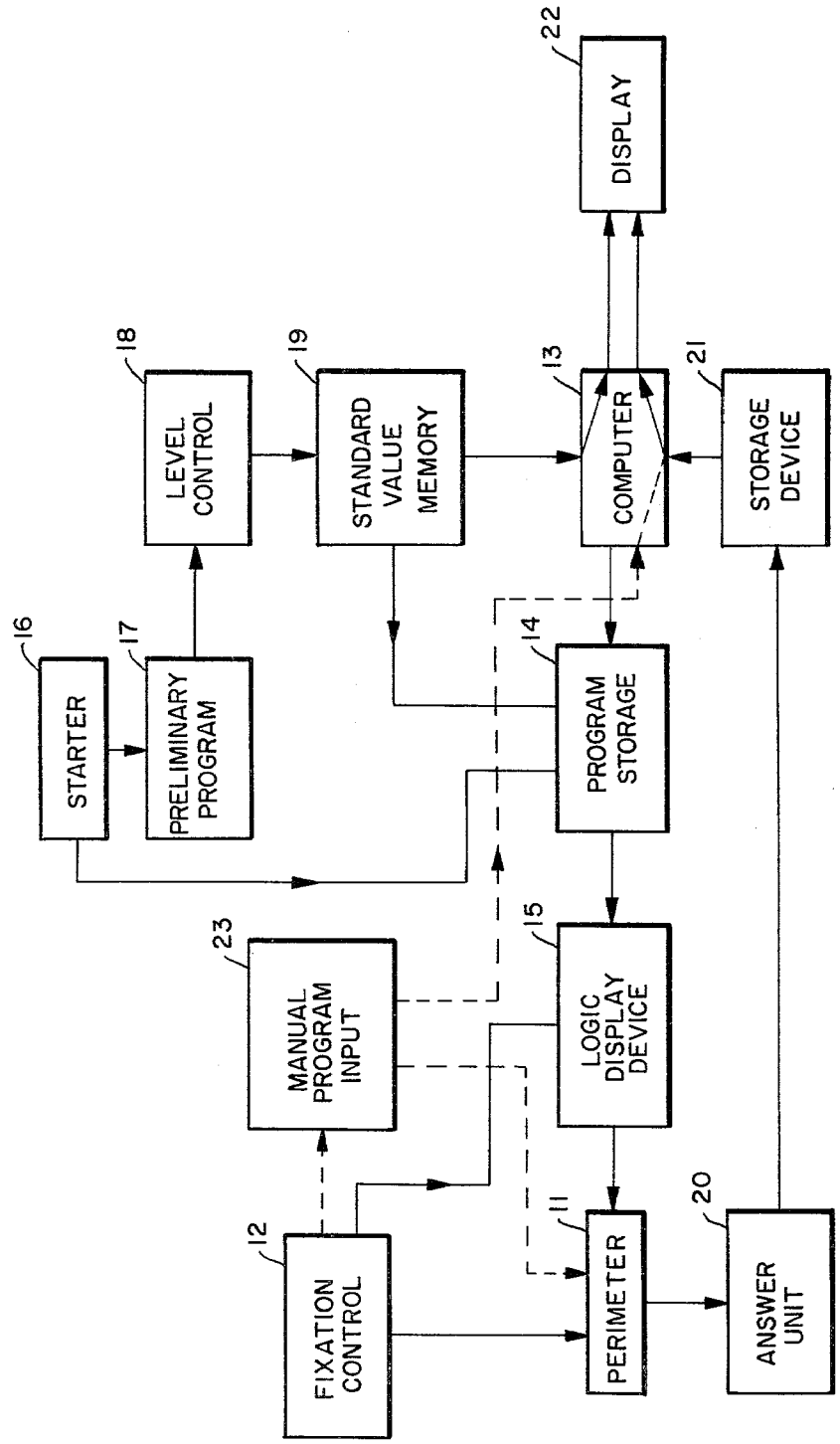
FIG. 5 is a block diagram of the apparatus according to the present invention.

FIG. 4 is a flow chart of the process of the present invention and FIG. 5 is a block diagram of the apparatus for carrying out the process. However, prior to conducting the process, it is necessary to store, in an electronic data storage device, a plurality of topographic sensitivity values of the human normal visual field. The thus-stored values which represent the standard values to be utilized must be distributed with regard to the number and position thereof over the entire visual field in a way so as to be acceptable from a medical viewpoint. Each of these stored standard values corresponds to a measuring point on the campimetric Bjerrum screen or the perimetric hemisphere as well as corresponding to a mean sensitivity distribution in the visual field under certain, defined measuring or testing conditions. This system of means sensitivity value distribution additionally requires a number of possibilities for variation considering the choice of testing conditions and the individual disposition of the patient to be tested.

With respect to the testing conditions, a choice must be made between photopical and mesopical surrounding field luminances. For example, if there are provided one photopic luminance and two mesopic luminances, e.g. at $10$ cd/m$^2$ and $10^{-1}$ or $10^{31\ 3}$ cd/m$^2$, respectively, in order to be able to test under three different adaptation luminances, then for each of these three luminances different values must be stored for the average standard sensitivity.

Additional variations of the stored standard values are necessary if the stimuli are offered at various sizes, durations, or colors. However, the stored data corresponds to the statistical mean value for a rather large collective group of patients, examined under the predetermined measuring conditions and demonstrating normal sensitivity distribution within the framework of a scattering width to be tolerated as shown by experience.

Also, the individual disposition of the patient requires a variation of the stored program, for example, for reasons of age. The scattering values of the individual normal or standard sensitivity as compared to the average normal sensitivity can be determined by pretesting the absolute sensitivity threshold, for which purpose a few values are sufficient, for example, 3 to 5 characteristic measuring points. The entire level of the stored average values is then correspondingly raised or lowered, depending on the previously measured, individual sensitivity threshold. The stored average standard normal values of eye sensitivity with their many variations thus represent a comprehensive data system and reference array, by means of which all subsequent measuring points or measuring curves of dynamic and static perimetry can be compared to one another.

The stored standard values can be retrieved individually or in programmed groups, for example, as intersecting curves of axially parallel or vertically oriented planes with regard to the the mountain range of eye sensitivity, and can then be recorded on measuring sheets. In this way, profiled sections or isopters are obtained for the average eye sensitivity and can serve as reference illustrations for the individual measurements to be conducted in the same way or direction. Moreover, by displaying the individually measured curves and the reference curves on the same measuring data sheet, there result directly visible and evaluatable difference values between the two curves.

As illustrated in FIG. 4, in step 1, the necessary adjustments for the patient to be tested is carried out which may include a fixation control. The process is started in step 2 and in step 3, a pretesting of the individual threshold values for the patient is carried out which may also include operation of a fixation control. In step 4, the values of the pretesting is set into a program register to adjust the program register to the individual threshold level. The program to be run is then selected from the storage device or memory in step 5 and the selected perimetry program is run in step 6 to effect a selected static or dynamic perimetry testing with fixation control. In step 7, the resultant measured values of the testing are stored and in step 8, a computer effects a comparison of the measured values with that of the corresponding stored standard for the selected program and individual test conditions with the deviations between the measured values and stored standard values being displayed in step 9 by a printer or the like in the form, for example, illustrated in FIGS. 1, 2 or 3 or in accordance with the program selected.

Further, the measured values obtained when conducting perimetry on patients can be stored on a program card or the like which may be used for documentation during subsequent comparative measurements during the course of a disease and which can be fed into the computer for display in a desired manner.

As illustrated in FIG. 5, the apparatus includes an automatic perimeter arrangement controlled by a computer which may be an Intel MDS 800 microprocessor of the type described in the "Octopus" brochure. As shown, there is provided a perimeter device 11, a fixation control 12, a computer 13 for controlling the perimeter device via a program storage device 14 and a logic display device 15. A starter control 16 is provided for conducting the process via a preliminary program device 17 and level controller 18 for providing the adjusting data for the standard values stored in the memory 19. In response to the testing, the patient may control answer unit 20 to a storage device 21 for storing measuring values. Both the memory 19 and the storage device 21 are connected with the computer 13, which compares the standard values corresponding to the test condition and the selected program with the measured values and provides an output to a display device 22, providing a display of the deviation between the measured and standard values.

The apparatus also includes a manual program input 23 which is coupled to the fixation control, perimeter device and computer as illustrated in dashed lines.

The reproduction of the measuring points on a display screen (Bjerrum screen or hemisphere) can take place either in a stationary manner, for example, with the aid of a controllable diode array according to German Pat. No. 2,507,723, or with the aid of a movable projector via mirror and prisms. In either case, the program devices, computer, storage devices, and memory are utilized to introduce and evaluate the measuring programs. In case of the stationary stimulus presentation, the volume of information depends on the density of covering the display screen with measuring points. In case of projected, movable light points, it is possible to present practically at any location of the display screen a light stimulus and utilize same for measuring purposes. By manual control of the projector, any desired examination program can be pursued, as in the case, for example, in classical kinetic or dynamic perimetry.

When storing standard values, each case can only involve a discrete selection of retinal points, with the consequence that during dynamic examinations and/or in static perimetry, the reference points cannot be exactly pinpointed in every case, under certain section orientations. The computer can therefore form substitute values for comparison purposes at the missing measuring points, derived from adjacent values by interpolation. In this regard, standard values are stored for the right and left eyes, respectively. Additionally, the computer enables a small or limited number of measuring threshold values to be obtained which small number of values is utilized to calculate a curve for the entire eye sensitivity characteristics which exhibits only minimum deviations as compared to a curve obtained from actually measured values of the eye being tested.

The present invention provides a higher diagnostic safety and facilitates the evaulation of perimetric measuring results than prior processes and devices. While heretofore the examination results were generally recorded dot by dot on preprinted sheets and then connected to a closed curve and subjected to diagnostic evaluation, the present invention enables the determination of the values for eye sensitivity in the entire visual field with the aid of quantitative static methods, accumulated in the measuring value storage unit of the computer, and compared with the standard values. In this connection, the light stimuli can be presented in an irregular sequence and distribution in the visual field, under program control. The stored results of the measurements initially represent a matrix of values, which cannot be comprehended readily in such form, but can be evaluated by the computer and displayed in the manner indicated so as to provide an indication of the difference in values between the true sensitivity distribution and the normal sensitivity distribution of the eye, at least in certain zones or over the entire visual field.

It is understood that the present invention is not limited to the details shown and described herein, but is susceptible to numerous changes and modifications as known to those skilled in the art such that the present invention is intended to cover all such changes and modifications as are encompassed by the scope of the appended claims.

I claim:

1. A process for dynamic or static perimetry of a human eye comprising testing the eye, topographically measuring threshold values of eye sensitivity for the eye being tested, electronically comparing the measured values with stored standard values of eye sensitivity corresponding to the testing conditions, and indicating deviations between the measured values and the stored standard values.

2. A process according to claim 1, further comprising the step of recording the measured values in one of graphic and tabular form.

3. A process according to claim 1, wherein the step of indicating deviation includes displaying in one of graphical and tabular form the deviations.

4. A process according to claim 1, wherein the step of measuring values of eye sensitivity is effected in accordance with at least one predetermined testing program in at least one of predetermined zones and directions to provide a sensitivity distribution curve of the eye being tested.

5. A process according to claim 4, comprising the step of correlating each testing program with corresponding stored standard values.

6. A process according to claim 5, wherein a plurality of testing programs for effecting static and dynamic perimetry are provided.

7. A process according to claim 1, comprising the step of storing standard values corresponding to personal characteristics of the human whose eye is being tested.

8. A process according to claim 7, wherein the personal characteristics include at least one of the age and individual sensitivity level of the human.

9. A process according to claim 1, further comprising storing standard values arranged in accordance with statistical findings point-by-point at any interstitial width over the visual field of the right and left eyes, and electronically computing intermediate values between adjacent points.

10. A process according to claim 9, wherein the step of storing includes electronically storing standard values for the right and left human eyes, respectively.

11. A process according to claim 1, wherein the step of indicating deviations includes simultaneously displaying the measured values and the standard values in the same manner.

12. A process according to claim 11, wherein the measured values and standard values are displayed in at least one of a point-by-point manner and as curve trains with the deviations being indicated by the standard values being displayed one of above and below the measured values.

13. A process according to claim 1 or 12, wherein the step of measuring threshold values includes obtaining a small number of measured values, and further comprising electronically calculating a curve for the entire sensitivity characteristic of the eye being tested and displaying the calculated curve.

14. A process according to claim 13, wherein the calculated curve exhibits minimum deviations as compared to the measured sensitivity characteristic for the eye being tested.

15. Apparatus for dynamic or static perimetry of a human eye comprising perimeter testing means for testing the eye and providing topographically measured threshold values of eye sensitivity for the eye being tested, comparing means for electronically comparing the measured values with stored standard values of eye sensitivity corresponding to the testing conditions, and means for indicating deviations between the measured values and the stored standard values.

16. Apparatus according to claim 15, further comprising means for automatically controlling the perimeter testing means in accordance with at least one predetermind testing program, and storing means for storing the standard values, each predetermined testing program being correlated with corresponding standard values.

17. Apparatus according to claim 16, wherein the indicating means includes display means for displaying the measured values and the standard values in at least one of graphical and tabular form.

18. Apparatus according to claim 17, wherein the display means simultaneously displays the measured values and the standard values in one of a point-by-point manner and as curve trains with deviations being indicated by displacement of the values with respect to one another.

* * * * *